United States Patent
Kuhn et al.

(10) Patent No.: US 6,499,221 B1
(45) Date of Patent: Dec. 31, 2002

(54) SETTING GAUGE FOR SETTING A DEPTH STOP ON A HANDPIECE FOR MEDICAL PURPOSES

(75) Inventors: Bernhard Kuhn, Schemmerhofen (DE); Bernhard Schilling, Attenweiler (DE)

(73) Assignee: Kalenbach & Voigt GmbH & Co, Biberach (DE)

( * ) Notice: Subject to any disclaimer, the term of this patent is extended or adjusted under 35 U.S.C. 154(b) by 0 days.

(21) Appl. No.: 09/527,591

(22) Filed: Mar. 17, 2000

(30) Foreign Application Priority Data

Apr. 9, 1999 (DE) .......................................... 199 16 114

(51) Int. Cl.[7] ............................................... A61C 3/00
(52) U.S. Cl. .............................. 33/514; 33/833; 433/75
(58) Field of Search ......................... 33/514, 513, 512, 33/549, 832, 833; 433/72, 75, 102, 224

(56) References Cited

U.S. PATENT DOCUMENTS

| | | | | |
|---|---|---|---|---|
| 3,346,959 A | * | 10/1967 | Fridge | 433/76 |
| 3,838,517 A | * | 10/1974 | Michnick | 433/72 |
| 4,165,562 A | * | 8/1979 | Sarfatti | 433/75 |
| 4,217,098 A | * | 8/1980 | Garnier | 433/147 |
| 4,512,081 A | * | 4/1985 | Park | 33/27.03 |
| 4,571,183 A | * | 2/1986 | Nash | 433/116 |
| 4,710,075 A | * | 12/1987 | Davison | 408/202 |
| 4,760,847 A | * | 8/1988 | Vaillancourt | 606/185 |
| 4,778,387 A | * | 10/1988 | Komatsu | 433/116 |
| 5,382,120 A | * | 1/1995 | Parsons | 408/16 |
| 5,465,492 A | * | 11/1995 | Bond | 33/275 R |
| 5,888,034 A | * | 3/1999 | Greenberg | 408/115 R |
| 6,213,770 B1 | * | 4/2001 | Kuhn | 433/75 |
| 6,213,771 B1 | * | 4/2001 | Fischer | 433/75 |
| 6,390,814 B1 | * | 5/2002 | Gardiner | 433/75 |
| 2002/0018979 A1 | * | 2/2002 | Matsutani et al. | 433/116 |

FOREIGN PATENT DOCUMENTS

| | | |
|---|---|---|
| DE | 40 17 038 A1 | 4/1991 |
| DE | 92 03 284 U1 | 8/1993 |

* cited by examiner

Primary Examiner—Diego Gutierrez
Assistant Examiner—R. Alexander Smith
(74) Attorney, Agent, or Firm—Fitzpatrick, Cella, Harper & Scinto

(57) ABSTRACT

The invention relates to a setting gauge (21) for setting a depth stop (6) on a handpiece (1), which has a connection device (3) for the releasable connection of a pin-shaped tool (4) with the handpiece (1), in particular for setting a depth stop (6) on a handpiece (1) for a working of a root canal (W2) in a tooth (Z). So that the setting of the depth stop can be effected more simply and with little manual effort, the setting gauge (21) has a connection element for connecting and positioning the setting gauge (21) on the handpiece (1) and at least one scale (27a, 27b, 27c) on the setting gauge body (22) which, in the position of the setting gauge (21) connected with the handpiece (1), extends parallel to the depth stop (6) and its setting path.

11 Claims, 3 Drawing Sheets

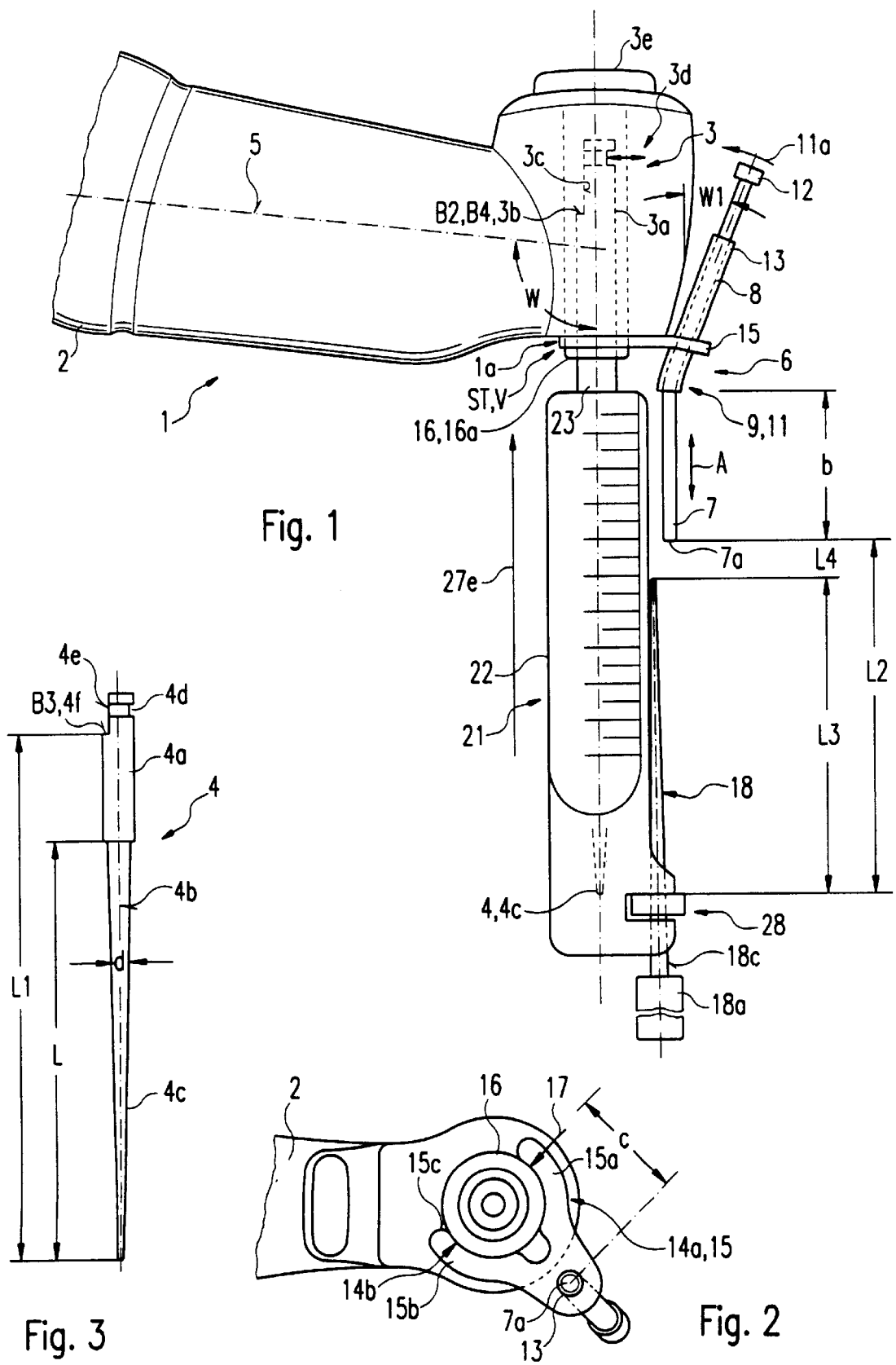

SETTING GAUGE FOR SETTING A DEPTH STOP ON A HANDPIECE FOR MEDICAL PURPOSES

BACKGROUND OF THE INVENTION

1. Field of the Invention

The invention relates to a setting gauge for setting a depth stop on a handpiece for medical purposes, in particular a handpiece for treating a root canal in a tooth.

2. Description of the Related Art

An above-mentioned handpiece serves, with a tool at its forward end that is effective to remove material, to produce or to prepare drilled holes or cavities in a body, whereby the body may be a part of a human or animal body, or a model for the human or animal body. In the first mentioned case, the handpiece is a medical or dental handpiece. In the second case, there is involved a handpiece for a medical, in particular dental, laboratory in which models or prostheses for parts for a human or animal body, e.g. dental prostheses, are produced.

In many treatment procedures with a handpiece of the present kind, it is of significance that a particular depth of a drilled hole or a cavity is not exceeded, in order e.g. not to penetrate through the wall of the body containing the drilled hole or the cavity. The present problem is of significance in particular in the preparation of root canals in teeth. On the one hand it is possible that a root canal is very strongly curved; that is, that an associated root canal tool does not follow the curvature and therefore requires a restriction of the working depth, so that the root canal tool does not penetrate through the wall of the root canal. A comparable problematic situation arises in the preparation of a conventional root canal which is to be worked with an associated root canal tool up to the so-called apex, whereby however the root canal tool should not be pushed in beyond the apex, since on the one hand this is painful for the patient and on the other hand adversely affects the jaw.

With a known procedure, the depth of the cavity of the drilled hole, or of the root canal, is determined e.g. with the aid of an X-ray image, and a depth stop arranged on the handpiece is so set that it bears against the body to be worked when the tool has reached its maximum working in depth. For the purpose of setting the depth stop on the handpiece there have already been developed setting gauges of various configurations. In accordance with one proposal, the setting gauge is formed by means of a rod-shaped measurement or setting body, on the peripheral surface of which there is provided an axially extending scale. With this setting gauge, a depth stop on the handpiece can be set or checked, in the presence of the tool mounted in the handpiece, in that the setting gauge with its stop surface is manually so applied in the axial direction of the tool or of the scale to the depth stop of the handpiece, and thereby manually held, that the tool extends parallel to the scale, so that its length can be read by means of the comparison of the tool tip with the measuring rod, and can be set by means of an alteration of the depth stop. In the employment of this setting gauge, handling is difficult because both the handpiece and the setting gauge are to be manually held and moved with respect to one another, which is not simple, whereby furthermore a manual alteration of the depth stop is to be effected, which even with the use of two hands of the operating person is difficult.

SUMMARY OF THE INVENTION

The object of the invention is to so configure a setting gauge of the kind concerned that a checking or setting of the depth stop can be effected with slight manual effort and more simply.

This object is achieved, according to one aspect of the invention, by means of a handpiece in which a driven end of a tool can be releasably attached so as to extend along an axis to a working end thereof, a stop device mounted on the handpiece for adjustable movement in a direction parallel to the axis and a setting gauge configured to bear against a reference surface on the handpiece and to be removable therefrom and having measures arranged thereon to indicate the position of the stop device along the axis.

According to other aspects, the invention involves a novel setting gauge for setting a moveable depth stop on a handpiece which has a connection device for the releasable connection of a pin-shaped tool for working of a root canal in a tooth, wherein the tool extends in the direction of movement of the depth stop. This novel setting gauge comprises a surface which is bearable against a corresponding surface of the handpiece, a mounting means for mounting the setting gauge on the handpiece to extend parallel to the depth stop, with the bearing surface bearing against a corresponding surface of the handpiece, and at least one scale having markings which represent increasing values in a direction toward s an end of the gauge which corresponds to the handpiece when the gauge is mounted thereon. In one of these other aspects the scale values correspond to the length of the tool which project beyond the depth stop. In another of these other aspects, further scales are provided which have markings corresponding to the lengths of other tools which project beyond the depth stop, those other tools being of different lengths. Advantageous further developments of the invention are described and claimed herein.

The setting gauge in accordance with the invention according to a particular aspect of the invention has a connection element for connecting and positioning the setting gauge on the handpiece in its functional disposition, in which the depth stop can be set on the scale. By this means, the setting gauge can be held on the handpiece so that no special manual grasping and holding of the setting gauge is needed; it can be held together with the handpiece in one hand or can be used in a disposition with the handpiece laid on a supporting surface. Further, in the disposition mounted on the handpiece, the scale on the base body is located in the vicinity of the depth stop, so that this can e.g. be set or pushed out or pushed in, in simple manner with sufficient exactitude.

The configuration according to the invention in accordance with a further aspect of the invention makes possible a setting of the penetration depth of the tool without consideration of the position of the tool or a tip, whereby the depth stop can be set directly on the scale. It is thus not necessary to connect the tool with the handpiece before the setting of the depth. The tool can also be connected with the handpiece after the setting of the depth. By this means, the setting gauge can be positioned on the handpiece more simply and more readily, whereby sufficient space for the setting gauge is also present since the space that the tool would occupy in the vicinity of the depth stop can be taken up by the setting gauge. By these means, a substantial simplification of the manipulation and setting of the depth stop is attained.

Within the scope of the invention it is possible, for determining the scale value which is to be set, to employ an assisting tool with which at least a part of the depth of the cavity to be worked, or of the root canal to be worked, can be measured and transferred to the scale. Thereby, the entire depth does not need to be measured; rather, it is also possible that only a part of the depth is measured, whereby the remaining depth can be determined in another manner, e.g.

by means of an X-ray image. These steps lead to the advantage that depths which develop in a curved manner, as is often the case with a root canal, can be more exactly determined.

With both configurations in accordance with the invention it is advantageous to arrange on the base body of the setting gauge a plurality of scales neighbouring one another, which are each associated with a particular tool length. Thereby, the setting of the depth stop is to be carried out on the scale which corresponds to the length of the tool located in the handpiece. In each case the scales are correspondingly positioned and distributed on the base body.

The setting and reading of the scale or scales is simple and reliable, in particular if the at least one scale is formed as a measure and is in particular provided with numbering, whereby the scale may have mm divisions formed by marks, at steps of 1 or 1.5 mm.

In its more specific aspects, the invention leads to simple and economically manufacturable configurations of compact construction, which can be manually handled simply and further improve the visual observation and the handling and holding of the setting gauge on the handpiece.

BRIEF DESCRIPTION OF THE DRAWINGS

Below, the invention and further advantages which can be achieved thereby will be described with more detail with reference to preferred embodiments and simplified drawings. There is shown:

FIG. 1 the forward end region of a medical or in particular dental handpiece, having a depth stop and a setting gauge mounted on the handpiece, in a side view;

FIG. 2 the forward end of the handpiece, in a view from below;

FIG. 3 an elevational view of a tool for the handpiece of FIGS. 1 and 2;

DETAILED DESCRIPTION OF THE PREFERRED EMBODIMENTS

Figures 4, 5, 7, 8:
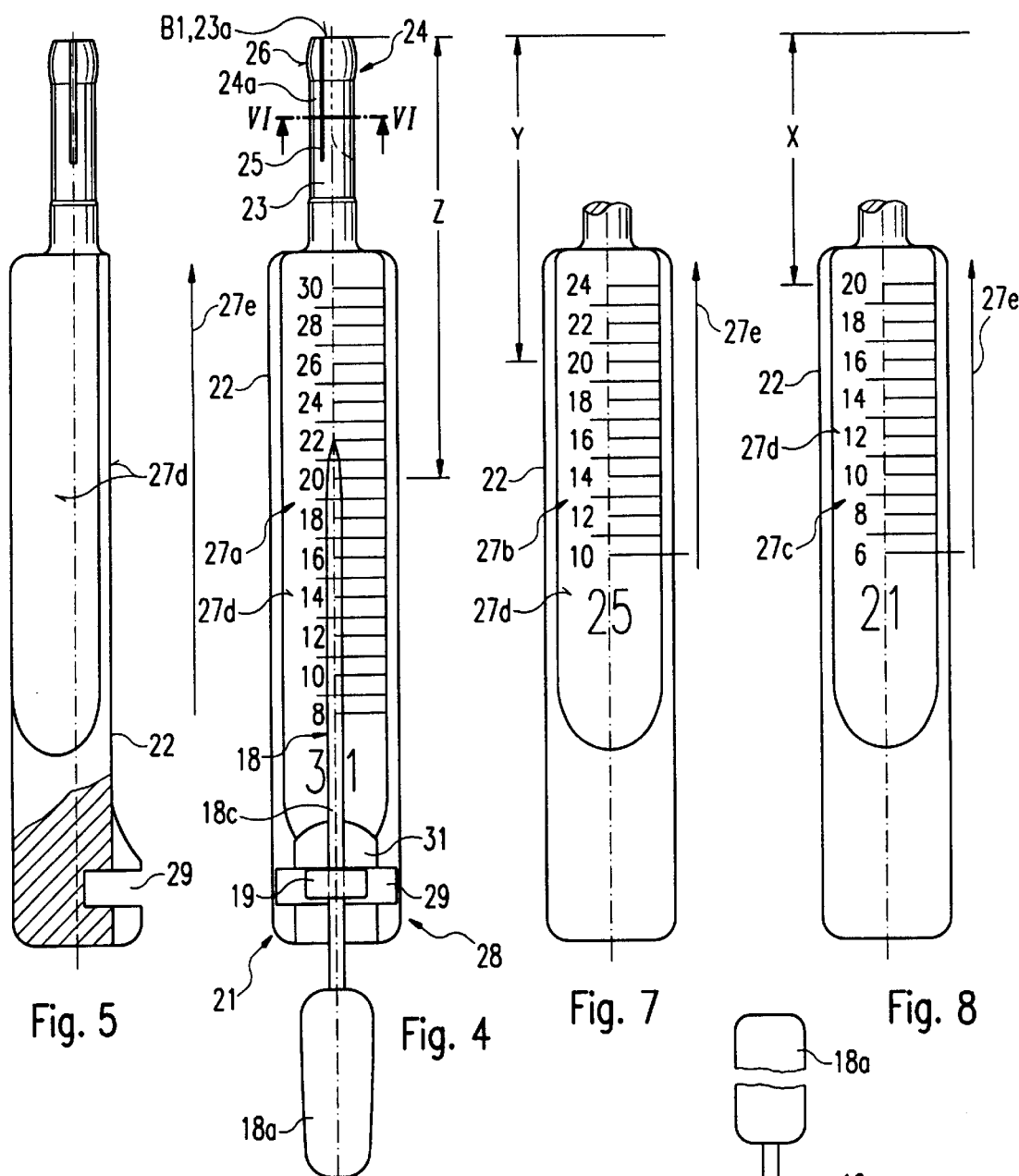
FIG. 4 a side elevational view of the setting guage of FIGS. 1 and 2 with a root canal tool to be manually operated.
FIG. 5 the setting gauge according to FIG. 4, in a side view from the left rotated by 90°.
FIG. 7 the setting gauge according to FIG. 4 in a side view rotated by 120°.
FIG. 8 the setting gauge according to FIG. 4 in a side view rotated by 240°.
Figure 6:
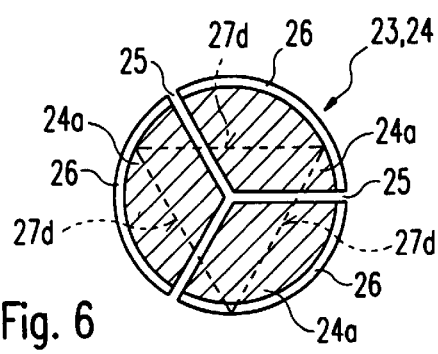
FIG. 6 the cross-section VI—VI of FIG. 4.

The handpiece 1, having the forward end region according to FIG. 1, has a grip sleeve 2 which may extend in a straight or angled manner, as is usual with dental handpieces, and which at its forward end integrates a connection device 3, e.g. a chuck or holding device for a machine or power tool 4 illustrated only in FIG. 3, which may be e.g. a material removing tool 4 having a shaft 4a which can be inserted and releasably connected in a lateral (FIG. 1) or forward (not shown) open connection hole 3a in the handpiece body 1a or handpiece head. In the present configuration, the elongate tool 4 extends transversely to the longitudinal middle axis 5 of the handpiece. A handpiece 1 which is angled is called in the art and angled head. Within the scope of the invention the connection device 3 or the tool can, however, also extend forwardly longitudinally of the middle axis 5 of the handpiece. The longitudinal middle axis 4b of the tool 4 and the longitudinal middle axis 5 of the handpiece 1 may include an approximately right-angle or an obtuse angle W, e.g. of about 90° to 150°, in particular about 105°, or may align with one another.

Figure 9:
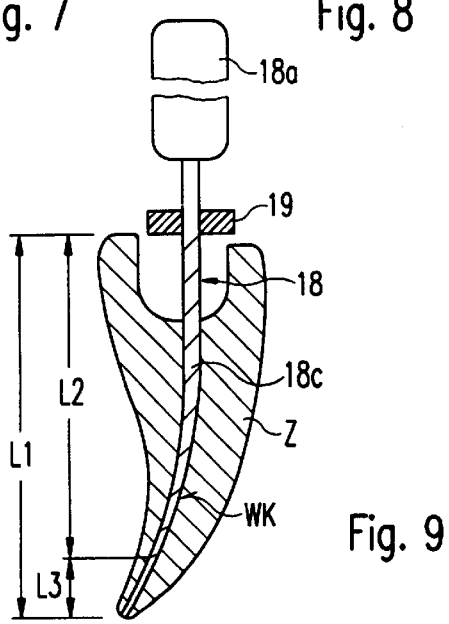
FIG. 9 a tooth in longitudinal section, with a root canal tool to be operated manually introduced into its root canal.

A drive device for the tool 4 is arranged in the handpiece 1. This may be a drive shaft train (not shown) which upon coupling of a rearward end of the grip sleeve 2 to a so-called connection part is connected directly or indirectly with a motor arranged in the connection part. The handpiece 1 may also be a so-called turbine, having a turbine drive in the forward end region of the handpiece 1 which is fed with compressed air from a supply line, which upon the above-described coupling of the grip sleeve to the connection part is coupled with an associated supply line section. In the present exemplary embodiment, the tool 4 is a thin and relatively long flexible root canal tool, which serves for the preparation of the root canal WK of a tooth Z (FIG. 9). A depth stop having a stop device 6 with a pin-shaped stop part 7 is releasably attached to the handpiece 1, the forward end region of the stop part being arranged to the side in the vicinity of the tool 4 and set back from its forward end, and forming a stop 7a.

The main parts of the stop device 6 are the stop parts 7 in the form of a pin having preferably round cross-section, a guide 8 in which the stop part 7 is arranged and is longitudinally displaceable, as indicated by the double headed arror A, an elastically effective clamping device 9 which exercises a transversely directed clamping force on the stop part 7 which is at least so great that in the functional operation it can take up stop forces effective against the stop part 7 without the stop part 7 being displaced into the guide 8, and on the other hand is only so great that the stop part can be manually grasped and displaced in the guide 8 by means of the exercise of a certain pushing or pulling force. Thereby, the transversely directed elastic clamping force, indicated by the arrow 11a, is overcome. In order to facilitate the manual grasping of the stop part 7, this has in an end region a waist or a thickening, e.g. a thickened head 12, preferably at the end of the stop part away from the tool tip. It consists of a relatively hard material, which due to its elongate or pin-like form is transversely elastically bendable, preferably of plastics, in particular of temperature resistant plastics.

The guide 8 is formed by means of an angled tube 13, to the inner cross-sectional size of which the stop part 7 is adapted with a slight play for movement, so that it is readily manually displaceable in a section of the tube 13 extending in a straight fashion. Due to the angling of the tube, e.g. by an angle W1 of about 30°, the straight stop parts 7 is compelled to take up an angled shape, i.e. upon pushing into the tube 13, the stop part 7 is bent into the angled shape. By this means, a return bending force 1a is brought about in the stop part 7 due to its elasticity, which presses constantly against the tube wall and thereby due to the surface friction present generates the elastic clamping force 11, whereby the bent limb the stop part 7 itself acts as transversely moveable clamping part. The magnitude of the clamping force 11 is dependent upon the angle W1 and/or upon the inner diameter of the guide 8 or the tube 13 and the transverse dimension of the stop part 7 and can be predetermined by means of a greater or smaller angle W1 and/or by a suitable selection of the inner and outer cross-sectional dimensions in the manner of a suitable mounting. The angling of the tube 13 is, in the apex region, preferably not sharp but rounded or curved.

The stop device 6 is connected with the handpiece 1 by means of a releasable quick-fastening connection, which is preferably formed by means of a plug-in/clamping device ST or a latching device V. For this purpose there are arranged on the stop device 6 a device part 14a and on the handpiece 1 a device part 14b which are elastically latchable with one another, whereby upon latching together and upon unlatching in each case one of the two latch parts is elastically outwardly bendable and thereby overcome with a certain application of force.

With the present configuration, the device part 14a of the clamping part is formed by means of a C-shaped clasp 15 having two claw-shaped arranged clasp arms 15a, 15b of elastically bendable material, which can be transversely pushed onto a for example cylindrical holding pin 16 on the handpiece 1, whereby upon pushing on the clasp arms 15a, 15b are first spread apart and then engaged behind the holding pin 16 and press against the holding pin 16. By these means there is generated a radially inwardly directed clamping force, which due to the friction restricts a rotation of the stop device 6 around the holding pin 16. only with a somewhat increased manual rotating force can be clasp 15 be steplessly adjusted in the circumferential direction on the holding pin 16, whereby in each adjusted position it is secured in the respectively set rotational disposition due to its clamping force 17 (FIG. 2). Upon the transversely directed pushing onto the holding pin 16, the end faces of the holding arms 15a, 15b form oblique guide surfaces 15c. This clasp 15 may be formed in a sleeve shape or by means of a thin disk (FIG. 1).

The axial position of the stop device 6 is determined by means of its bearing on a shoulder surface 16a of the holding pin 16 of the handpiece 1.

The clasp 15 can be inserted transversely or axially onto the holding pin 16, whereby a corresponding hollow conical shaped end face of the holding pin 16 or a chamfering or rounding of the inner hole edge of the clasp 15 forms an guide surface facilitating the axial insertion.

The radially inwardly directed clamping force 17 of the latching or clamping device V, ST is so dimensioned that due to the clamping resulting therefrom an undesired rotation of the stop device 6 upon use of the handpiece is prevented. However, the stop device 6 can be rotated by means of the manual application of force, whereby the clamping 17 is overcome and is then self-actingly again effective in each steplessly settable rotation position. With the present configuration, the clasp arms 15a, 15b are inwardly rounded in the shape of a circular arc, whereby in the relaxed condition the radius is somewhat smaller than the diameter of the holding pin 16.

The tube 13 is attached to the clasp 15 on the one hand in its middle region or in the region of its angled apex and on the other hand in the region of the apex of the clasp 15.

In the disposition illustrated in FIG. 1 the stop part 7 is in a pushed on disposition. The spacing b present in this disposition up to the forward end of the guide tube 13 can serve as setting range. The tube 13 extends alongside the handpiece 2 and the stop part 7a extends at a radial spacing c from the middle axis of the connection hole 3a or of the tool 4, here alongside its angled head 1a, whereby the radial spacing c may be e.g. about 3 mm to 6 mm, in particular about 4 mm to 5 mm, which preferably develops parallel to the middle axis of the setting gauge 21 or its connection shaft 23.

With the present exemplary embodiment, the holding pin 16 is formed by means of a sleeve which surrounds a drive sleeve 16a which receives the shaft 4a of the tool 4.

There are associated with the handpiece 1 a plurality of tools 4 of different diameters d, which may have a diameter from e.g. 0.15 mm to 0.40 mm in steps of 0.05 mm, and can be characterized by means of a different colour marking in particular in the region of their shaft 4a. Further, the tools 4 are available in different lengths L of their working sections 4c, e.g. three tool 4 of different lengths, each with a length L of 21, 25 and 31 mm. The different lengths serve for working teeth or root canals of different lengths or depths. Thereby, an adaptation to root canals of different cross-sectional sizes is possible by means of the selection of a suitable tool 4. What is said above applies also for such tools which are not root canal tools, e.g. tools for the material removing working of drilled holes or of cavities, e.g. for receiving filings.

One or more hand tools 18 are also associated with the handpiece 1, which may be provided in the same length and diameter steps and may differ from the machine tools 4 through a different form of the shaft 18a.

There is also associated with the handpiece at least one disk-shaped or sleeve-shaped so-called stopper 19 FIGS. 4 and 9 of soft and/or elastic material, e.g. rubber or plastics, in which a small through-hole is present or which can be placed onto the tool 4 or 18, whereby due to the elasticity the stopper 19 is—in each pushed on position on the working section 4c, 18c of the tool 4, 18—arrested longitudinally by clamping effect, in a manner which can be overcome and thus is manually longitudinally movable with a certain application of force.

As shown in FIG. 3, a machine tool 4 has e.g. a cylindrical shaft 4a which for its axial connection with the connection device 3 has a first recess 4d, e.g. an annular groove, and for its rotational connection with the connection device 3 has a second recess 4e which extends only over a part of its circumference and with the present exemplary embodiment is formed by means of a flattening of the shaft 4a opening out at the end face. The shoulder surface 4f of the second recess 4e serves as a stop surface for limitation of the insertion movement of the machine tool 4 into the handpiece body 1a, whereby in the pushed-in position it bears on a counter shoulder surface 3b of a projection 3c in the connection hole 3a of the handpiece 2 (FIG. 1), which with the second recess 4e forms a rotation drive connection for the machine tool 4. For axial securing of the machine tool 4 a coupling part 3d is mounted transversely movably in the region of the drive sleeve 16a, which coupling part is manually moveable between a coupling position engaging into the first recess 4d and a decoupling position releasing the tool shaft 4a. For this purpose there serves an externally accessible actuating member 3e on the handpiece 1a, e.g. a press button, on the side of the handpiece body 1a opposite to the tool 4.

A hand tool 18 can, in contrast, as a rule have a shaft 18a which for the purpose of improving gripability has transverse grooves and with regard to it cross-sectional size is dimensioned to be larger and in the most cases can be of plastics.

The setting gauge 21 consists of an e.g. pin-shaped base body 22 and a pin-shaped connection shaft 23, the cross-sectional shape and/or size is adapted to the cross-sectional shape and size of the shaft 4b of a machine tool 4, so that the setting gauge 21 can be inserted with the connection shaft 23 into the connection hole 3a present in the connection device 3. Thereby, a form-fittingly effective connection at the connection shaft 23 is not needed, and thus the first recess 4d and the second recess 4e can be omitted, in order to simplify and facilitate operational handling. In order that the connection shaft 23 does not unintentionally fall out of its inserted position in the handpiece there is provided for its axial securing in the connection hole 3a a clamping device 24 (FIG. 1) arranged on the shaft 23, which presses against the wall of the receiving hole with a slight spreading effect and upon insertion and withdrawal of the setting gauge 21 is readily manually overcome. With the present exemplary embodiment the clamping device 24 is formed by means of two or three shaft segments 24a arranged opposite to one another, and which are separated from one another by means of thin radial slits 25, which run out at the free end of the connection shaft 23 so that the shaft segments 24a are connected at their inner ends with the connection shaft 23 and extend axially freely and thus radially springable outwardly and inwardly due to their elasticity. Thereby, the arrangement can be so effected that the free end of the shaft segments 24a, in their free initial disposition, take up a somewhat greater cross-section than the cross-section of the insertion hole of the connection device 3, whereby the connection pins 23 are slightly pressed together upon insertion and that by exercise the radial clamping force against the insertion hole wall. For the purpose of facilitating the insertion, the connection pins 23 are rounded at the outer edges in the manner of guide surfaces, or provided with chamfered surfaces. With the present exemplary embodiment, the connection shafts 23 have preferably at their free ends a small radial extension 26 on their outer surface which creates the cross-sectional enlargement, so that the connection shafts 23 can extend on themselves axially parallel and be separated from one another by means of equally thick slits 25.

The pin-shaped base body 22 has a plurality of axial scales 27a, 27b, 27c or measures (FIGS. 4, 6, 7 and 8), arranged distributed around the circumference, which although of like scale value divisions or measurement divisions, e.g. in mm, and may have marker lines at an interval of e.g. 0.5 mm, are different with regard to their scale values formed by markings or measurement numbers. Each measure 27a, 27b, 27c belongs to a particular length L or L1 of the tool 4. With the present exemplary embodiment three measures 27a, 27b, 27c are provided which are each associated with a commonplace tool length 31 mm, 25 mm and 21 mm. Within the scope of the invention, the measures may be arranged on the round outer surface of the base body 22. In the present exemplary embodiment, the measures 27a, 27b, 27c are each arranged on a secantial surface 27d. If three measures 27a, 27b, 27c are provided, the secantial surfaces 27d forms a triangular cross-sectional shape for the base body 22.

The secantial surfaces 27d may extend over the entire length of the base body 22. With the present exemplary embodiment they extend, starting from the end carrying the connection shaft 23, only over the larger part of the length of the base body 22, whereby they run out at a spacing from the forward end away from the connection shaft 23, in particular rounded, at the preferably cylindrical outer surface of the base body 21. The lengths of the secantial surfaces 27d may thereby be different. As FIG. 4 shows, the secantial surface 27d having a longest measure 27a for the tool of the greatest length, e.g. 31 mm, is longer than at least one of the other secantial surfaces 27d.

With the exemplary embodiment according to FIGS. 4 and 5, in the forward end region of the base body 22, a positioning device 28 is associated with one of the measures 27a, 27b, 27c, preferably with the longest measure 27a, which device allows a longitudinally and preferably also transversely effective positioning of the hand tool 18 in a position extending along and adjacent to or on the associated measure 27a. For the purpose of ready emplacement and removal of the tool 18, the positioning device 28 is accessible in the manner of a plug-in device. With the present exemplary embodiment, the tool 18 can be plugged-in transversely into the positioning device 28, whereby the stopper 19 constitutes the positioning element associated with the tool 18. The corresponding positioning element associated with the setting gauge 21 is formed by means of a lateral transverse groove 29, which is formed so wide and deep that the stopper 19 can be placed therein with slight play for movement and is axially positioned. For the purpose of transversely directed positioning there is provided in the region of the transverse groove a longitudinal groove 31 in the base body 22, which e.g. may have a rounded cross-sectional shape and which can be placed in the working region 18c of the tool 18. With the present exemplary embodiment, the longitudinal groove 31 is arranged in the region of material of the forward end of the base body 22 projecting beyond the associated secantial surface 27d.

As already with the machine tool 4, there is also provided for the setting gauge 21 or its base body 22 a stop surface 23a (FIG. 4) limiting the insertion movement into the handpiece body 1a, which is arranged in the end region of the setting gauge 21, towards which the scale values increase. This direction of the scale is indicated in FIG. 1 by the arrow 27e. The stop surface 23a, upon insertion into the handpiece body 1a, cooperates with a counter stop surface on the handpiece body 1a, whereby the insertion movement is limited. With the present exemplary embodiment the stop surface 23a is formed by means of the end surface of the shaft 23 and the counter stop surface is formed by means of the counter shoulder surface 3b in the connection hole 3a. A different stop surface and counter stop surface on the setting gauge 21 and on the handpiece body 1a is however also possible.

The scale or measures 27a, 27b, 27c are in each case arranged in a particular relationship to a first reference surface B1 (FIG. 4) on the setting gauge 21. In the condition of the setting gauge 21 or the base body 22 connected with the handpiece body 1a, the measures 27a, 27b, 27c stand also in a particular relationship to a second reference surface B2 (FIG. 1) on the handpiece body 1a, which corresponds to the first reference surface, here in the stop position. Thereby the measures 27a, 27b, 27c are so arranged with regard to the reference surfaces B1, B2 that a selectable scale or measure value corresponds a desired penetration depth of the machine tool, taking into account its length L or L1. Due to this configuration, in the functional disposition of the setting gauge 21, in which the reference surfaces B1, B2 correspond with one another or lie against one another, the depth stop 6 must merely be set with its stop surface 7a to a scale or measure value corresponding to the desired penetration depth L2. It should be taken into account that not only the setting gauge 21 but also the machine tool 4 have a reference marking formed by means of a reference surface B3 (FIG. 3), in this case the shoulder surface 4f, which cooperates with a fourth reference surface B4 (FIG. 1) on the handpiece body 1a, which in the present exemplary embodiment is identical with the second reference surface B2. The reference surfaces B2 and B4 may, however, also be arranged in an appropriate relationship on the handpiece body 1a. Consequently, the desired penetration depth L2 is provided by means of the setting of the depth stop 6 on the associated scale or measure 27a, 27b, 27c, without the need, after the mounting of the machine tool 4 on the handpiece body 1a, for its length to be set or even checked.

The respective dispositions of the scales associated with the different tool lengths can be determined taking into account the respective associated tool length L or L1. The greater the associated tool length L or L1, the greater also the longitudinal directed spacing of the associated scale or of the associated measure with regard to the reference point associated therewith. This can be particularly explained and recognized with reference to FIGS. 4 to 8. As reference point for the three measures 27a, 27b, 27c there are assumed e.g. the scales or measure values 20 (mm). with the smallest tool length L1, this exemplary reference point 20 has a spacing x (FIG. 8) from the reference surfaces B1 and B2. With the next longer machine tool 4 this spacing y (FIG. 7) is dimensioned greater by the length difference of the tool length L1. This applies also for the third tool length L1 according to FIG. 4, with which the corresponding spacing z is dimensioned to be greater in correspondence to the length difference L1.

With the configuration in accordance with the invention the desired penetration depth L2 can thus be set by a direct setting of the depth stop 6 on the associated scale. The length L1 associated with the machine tool 4, after its mounting, is automatically located in such a position that it projects beyond the stop surface 7a of the depth stop 6 by the penetration depth L2, see FIG. 1 in which is tip of the machine tool 4 is indicated by broken lines. The penetration depth L2 or, in the present exemplary embodiment, the root canal length, can be measured, e.g. on the basis of an X-ray image taking into account the respective scaling of the X-ray image.

Below, the functioning of the setting gauge 21 together with a setting of the stop device 6 for a particular penetration depth L2 of an associated machine tool will be described.

For a setting of the penetration depth there is first needed knowledge of the depth with which the tool 4 should penetrate into the object to be worked, here a tooth Z (FIG. 9) e.g. of the human body. In the present exemplary embodiment, namely in the working of a root canal WK, this depth is predetermined by the length L2 of the root canal WK or by the height of the tooth Z. These maximum penetration depths L2 to the apex should not be exceeded in particular in the working of a root canal WK by means of the tool 4.

For limiting this penetration depth L2 on the handpiece 1, the setting gauge 21 is connected with the handpiece 1 by insertion into the connection hole 3a and thus brought into its functional disposition. Thereby, the stop device 6 should be located adjacent the scale which is associated with the tool 4 with which the root canal WK is to be worked. If the penetration depth L2 is known or is estimated in advance, a correspondingly long tool 4 can be selected. Now, the stop part 7 is moved into a position in which its stop 7a coincides with the associated scale value, e.g. of the measure 27a for a tool 4 of the length L=31 mm, with a position of this measure 27a which corresponds to the penetration depth L2. Advantageously, the measures 27a, 27b, 27c are indicated by millimetre divisions and numbering, which corresponds to the possible penetration depth range, which in the case of the tooth is determined by possible tooth lengths. In the present exemplary embodiment, the stop 7a can be set to a measurement line of the measure 27a which is indicated by a number which—referred to the present tool length L or L1—corresponds to the penetration depth L2 in millimetres. After this setting, the setting gauge 21 can be removed from the handpiece 1 and the tool 4 with the associated length L1 can be placed into the handpiece 1. The length, indicated by broken lines in FIG. 1, with which the tool 4 projects beyond the stop 7a then corresponds to the maximum penetration depth L2. Such a measurement scale has increasing numeral values in the direction 27e on the connection shaft 23 or on the handpiece 1.

With the exemplary embodiment according to FIGS. 4, 7, 8 and 9, the maximum penetration depth L2 is determined with an assisting tool, e.g. a machine tool 4 or a hand tool 18 of small diameter d, which is inserted so far as possible into the root canal WK. With the stopper 19, the occlusal end of the tooth Z is indicated on the working section 18c of the tool, whereby a partial length, namely the length L3 of the penetration depth L2 is determined. The remaining length L4 directly before the apex can e.g. be determined by means of an X-ray image through X-raying of the tooth Z of the patient. The sum of the partial length L3 and the remaining length L4 yields the penetration depth L2. The assisting tool, prepared by means of the particular position of the stopper 19, is then placed in the positioning device 21 of the setting gauge 21, which is in place in the handpiece 1, and the position of the tool tip is read on measure 27a. The remaining length L4 is then summed with, here added to, this value and the stop 7a of the stop device 6 is set to the value then provided. After exchange of the setting gauge 21 with the machine tool 4 of the associated length L or L1, the tool tip (indicated in FIG. 1 by broken lines) then projects beyond the stop 7a by the penetration depth L2. In the working of the root canal WK, an insertion of the tool 4 beyond the apex is then prevented, because the stop 7a impacts against an occlusal surface of the tooth Z. The above-described adding-in of the remaining length L4 is particularly simple to carry out if the scale or measure division is sub-divided in mm indicators. Within in scope of the invention, however, other scale divisions are also possible.

The setting gauge 21 may also be of plastics of sufficient strength, in particular hard plastics or metal, whereby a light metal, in particular aluminium, is particularly well suited for weight saving reasons. Furthermore, in particular with the employment of aluminium, an advantageous surface coating can be attained by means of anodising.

Figure 10:
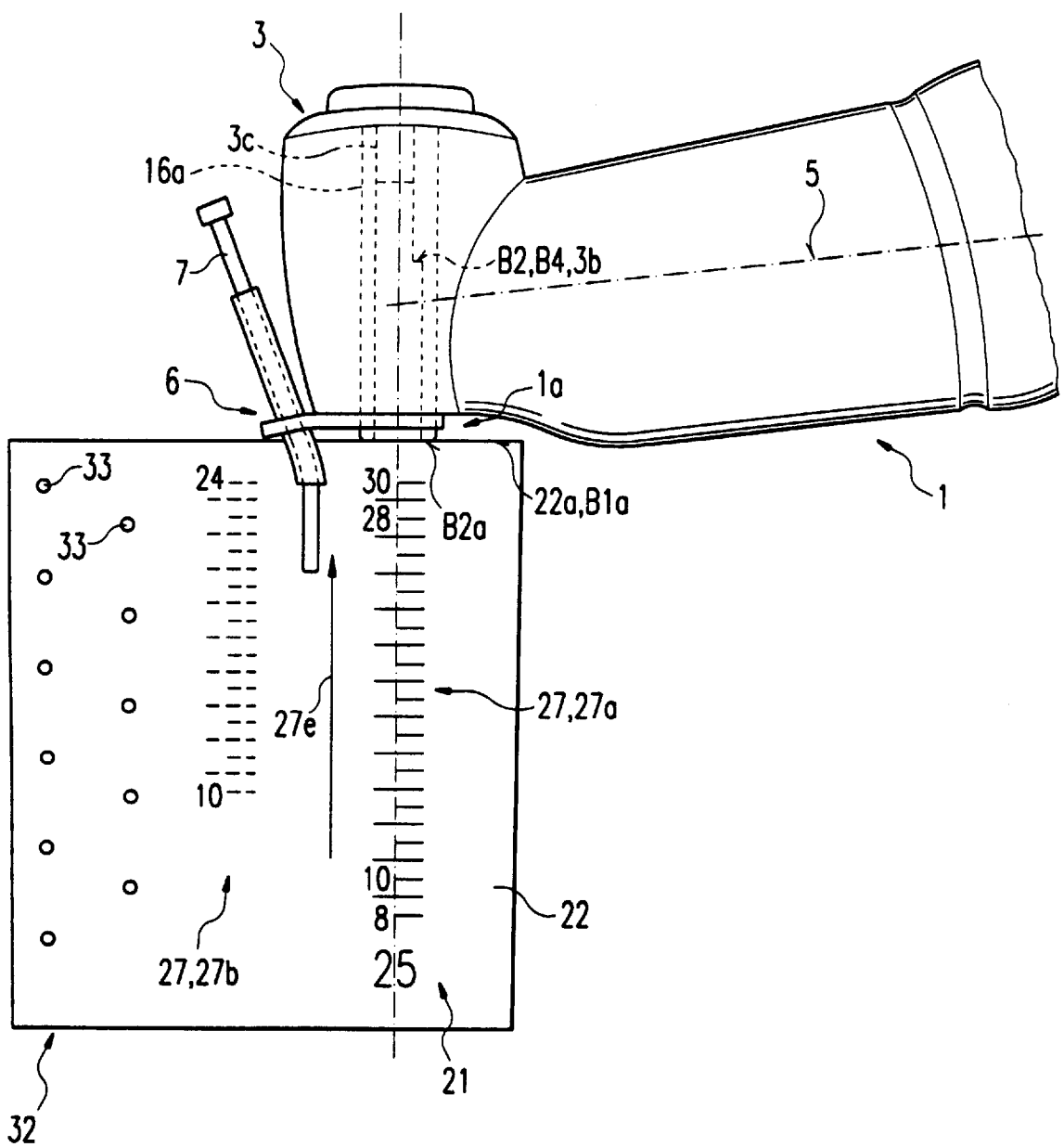
FIG. 10 a setting gauge in accordance with the invention, in correspondence disposition with a handpiece, in a modified configuration.

The exemplary embodiment according to FIG. 10, in which the same or similar parts are provided with the same reference signs, differs from the above-described exemplary embodiment in several respects. On the one hand, this exemplary embodiment makes it clear that the setting gauge 21 does not need to be a means which is connectable with the connecting device 3 of the handpiece 1. It is sufficient if the setting gauge 21 is brought into a coinciding reference position by means of two mutually corresponding reference elements, in which the depth stop 6 extends with its setting path parallel to the scale, here to at least one measure 27. This reference position can also be attained when an abutment is present between setting gauge 21 or base body 22 and the handpiece body 1a. With the exemplary embodiment according to FIG. 10, the setting gauge 21 bears with its base body 22 on an outer surface of the handpiece body 1a towards the setting gauge which outer surface may e.g. be formed by means of the end face of the drive sleeve 16a. Thereby, the base body 22 may, with an opposing surface, e.g. with its end face 22a, which forms a reference surface B1a, bears against the outer surface, e.g. the drive sleeve 16a, which forms a reference surface B2a, whereby the reference surfaces B1a, B2a stand in a relationship, corresponding to the above described exemplary embodiment, to the reference surfaces B3 and B4 on the machine tool 4 (FIG. 3) and on the handpiece body 1a. The corresponding reference surface B3 for the machine tool 4, in contrast, remains the counter shoulder surface 3b.

With the exemplary embodiment according to FIG. 10, only one scale or measure 27 is illustrated. Within the scope of the invention, however, there may also be arranged a plurality of parallel rules, e.g. 27a, 27b, with which the depth stop 6 can cooperate, in particular if they are located to the two sides of the depth stop 6.

The exemplary embodiment according to FIG. 10 further makes clear that the setting gauge 21 may also be arranged in the region of parts of the workstation present, e.g. on a carrier 32 for tools 4 or 18, which are insertable into receiving holes 32 on the upper side of the carrier 33 and thus can be deposited in an ordered manner in the vicinity of the work or treatment station.

What is claimed is:

1. Apparatus for setting a moveable depth stop, said apparatus comprising:
    a handpiece on which said moveable depth stop is mounted, and which has a connection device for the releasable connection of a pin-shaped tool for working of a root canal in a tooth, wherein said tool extends in the direction of movement of said depth stop,
    a setting gauge having a surface which is bearable against a corresponding surface of said handpiece;
    mounting means for mounting said setting gauge on said handpiece to extend parallel to said depth stop, with said bearing surface bearing against a corresponding surface of said handpiece;
    at least one scale having markings which represent increasing values in a direction towards an end of said gauge which corresponds to said handpiece when said gauge is mounted thereon;
    a first reference marking associated with said scale and being positionable in correspondence with a corresponding reference marking on said handpiece when said bearing surface bears against said corresponding surface of said handpiece; and
    said scale values corresponding to the length of said tool which projects beyond said depth stop.

2. Apparatus according to claim 1, wherein the scale values are arranged in such correspondence to a reference element which is positionable in correspondence with said handpiece reference marking that the scale values correspond to the length of said tool which projects beyond the depth gauge;
    at least one scale having markings which represent increasing values in a direction towards an end of said gauge which corresponds to said handpiece when said gauge is mounted thereon;
    a first reference marking associated with said scale and being positionable in correspondence with a corresponding reference marking on said handpiece when said bearing surface bears against said corresponding surface of said handpiece; and
    said scale values corresponding to the length of said tool which projects beyond said depth stop.

3. Apparatus according to claim 2, wherein a plurality of scales are provided on the setting gauge, each of said scales corresponding to a different tool length.

4. Apparatus according to claim 3, wherein said scales are arranged to be evenly distributed about the outer surface of a body of said setting gauge.

5. Apparatus according to claim 2, wherein said reference markings are formed by mutually facing surfaces on the setting gauge and on the handpiece.

6. Apparatus according to claim 2, wherein the setting gauge has a connection element in an end region towards the reference marking thereon for connecting and positioning said setting gauge on said handpiece.

7. Apparatus according to claim 6 and further including a securing device for securing said connection element against unintended release.

8. Apparatus according to claim 1, wherein said setting gauge is constructed to be freely rotatable around an axis thereof which extends parallel to said direction of movement of said depth stop.

9. Apparatus according to claim 1 and further including an assisting tool configured such that one end thereof is insertable into a tooth cavity and which is positionable to extend along said scale such that its said one end faces in the direction in which said scale values increase.

10. Apparatus for setting a moveable depth stop, said apparatus comprising:
    a handpiece on which said moveable depth stop is mounted, and which has a connection device for the releasable connection of a pin-shaped tool for working of a root canal in a tooth, wherein said tool extends in the direction of movement of said depth stop,
    a setting gauge having a surface which is bearable against a corresponding surface of said handpiece;
    mounting means for mounting said setting gauge on said handpiece to extend parallel to said depth stop, with said bearing surface bearing against a corresponding surface of said handpiece;
    at least one scale having markings which represent increasing values in a direction towards an end of said gauge which corresponds to said handpiece when said gauge is mounted thereon;
    said scale values corresponding to the length of said tool which projects beyond said depth stop; and
    further scales having markings which correspond to the lengths of other tools which project beyond said depth stop, said other tools being of different lengths.

11. Apparatus according to claim 10, wherein said setting gauge has a connection shaft which fits into said connection device in said handpiece for connection thereto.

* * * * *